(12) United States Patent
Egashira (10) Patent No.: US 10,568,860 B2
(45) Date of Patent: Feb. 25, 2020

(54) PHARMACEUTICAL COMPOSITION CONTAINING STATIN-ENCAPSULATED NANOPARTICLE

(75) Inventor: Kensuke Egashira, Fukuoka (JP)

(73) Assignees: KOWA CO., LTD., Nagoya-shi (JP); SENTANIRYOUKAIHATSU CO., LTD., Fukuoka-shi (JP)

( * ) Notice: Subject to any disclaimer, the term of this patent is extended or adjusted under 35 U.S.C. 154(b) by 0 days.

(21) Appl. No.: 12/310,619

(22) PCT Filed: Aug. 30, 2007

(86) PCT No.: PCT/JP2007/066926
§ 371 (c)(1),
(2), (4) Date: Mar. 2, 2009

(87) PCT Pub. No.: WO2008/026702
PCT Pub. Date: Mar. 6, 2008

(65) Prior Publication Data
US 2010/0086602 A1   Apr. 8, 2010

Related U.S. Application Data (60) Provisional application No. 60/840,950, filed on Aug. 30, 2006.

(51) Int. Cl.
*A61K 31/22*   (2006.01)

(52) U.S. Cl.
CPC .................................... *A61K 31/22* (2013.01)

(58) Field of Classification Search
CPC .............................. A61K 31/22; A61K 9/5153
See application file for complete search history.

(56) References Cited

U.S. PATENT DOCUMENTS

| | | | |
|---|---|---|---|
| 3,773,919 A * | 11/1973 | Boswell et al. | A61K 9/1647 424/486 |
| 4,231,938 A | 11/1980 | Monaghan et al. | |
| 4,346,227 A | 8/1982 | Terahara et al. | |
| 4,444,784 A | 4/1984 | Hoffman et al. | |
| 4,739,073 A | 4/1988 | Kathawala | |
| 4,897,402 A | 1/1990 | Duggan et al. | |
| 4,904,646 A | 2/1990 | Karanewsky et al. | |
| 4,906,624 A | 3/1990 | Chucholowski et al. | |
| 4,906,657 A | 3/1990 | Roth | |
| 4,920,109 A | 4/1990 | Onishi et al. | |
| 4,923,861 A | 5/1990 | Picard et al. | |
| 4,929,620 A | 5/1990 | Chucholowski et al. | |
| 4,939,143 A | 7/1990 | Regan et al. | |
| 4,940,727 A | 7/1990 | Inamine et al. | |
| 4,940,800 A | 7/1990 | Bertolini et al. | |
| 4,946,860 A | 8/1990 | Morris et al. | |
| 4,946,864 A | 8/1990 | Prugh et al. | |
| 4,950,675 A | 8/1990 | Chucholowski | |
| 4,957,940 A | 9/1990 | Roth | |
| 4,963,538 A | 10/1990 | Duggan et al. | |
| 4,968,693 A | 11/1990 | Joshua et al. | |
| 4,970,231 A | 11/1990 | Lee et al. | |
| 4,992,429 A | 2/1991 | Ullrich et al. | |
| 4,994,494 A | 2/1991 | Regan et al. | |
| 4,996,234 A | 2/1991 | Regan et al. | |
| 4,997,837 A | 3/1991 | Chucholowski et al. | |
| 5,001,128 A | 3/1991 | Neuenschwander et al. | |
| 5,001,144 A | 3/1991 | Regan et al. | |
| 5,017,716 A | 5/1991 | Karanewsky et al. | |
| 5,021,453 A | 6/1991 | Joshua et al. | |
| 5,025,000 A | 6/1991 | Karanewsky | |
| 5,081,136 A | 1/1992 | Bertolini et al. | |
| 5,091,378 A | 2/1992 | Karanewsky et al. | |
| 5,091,386 A | 2/1992 | Kesseler et al. | |
| 5,098,931 A | 3/1992 | Duggan et al. | |
| 5,102,911 A | 4/1992 | Lee et al. | |
| 5,112,857 A | 5/1992 | Vickers | |
| 5,116,870 A | 5/1992 | Smith et al. | |
| 5,130,306 A | 7/1992 | Duggan et al. | |
| 5,132,312 A | 7/1992 | Regan et al. | |
| 5,135,935 A | 8/1992 | Alberts et al. | |
| 5,166,171 A | 11/1992 | Jendralla et al. | |
| 5,182,298 A | 1/1993 | Helms et al. | |
| 5,196,440 A | 3/1993 | Bertolini et al. | |

(Continued)

FOREIGN PATENT DOCUMENTS

| | | |
|---|---|---|
| WO | 99/18952 | 4/1999 |
| WO | 01/93806 | 12/2001 |

(Continued)

OTHER PUBLICATIONS

Roche, Victoria F.; "Antihyperlipidemic Statins: a Self-Contained, Clinically Relevant Medicinal Chemistry Lesson", 2005, American Association of Colleges of Pharmacy, The American Journal of Pharmaceutical Education, vol. 69, No. 4, Article 77, pp. 546-560.*

Feringa, Harm H. H. et al.; "The effects of intensified lipid-lowering therapy on long-term prognosis in patients with peripheral arterial disease", 2007, The Society for Vascular Surgery, Journal of Vascular Surgery, vol. 45, pp. 936-943.*

Schanzer, Andres et al.; "Statins are independently associated with reduced mortality in patients undergoing infrainguinal bypass graft surgery for critical limb ischemia", 2008, The Society for Vascular Surgery, Journal of Vascular Surgery, vol. 47, pp. 774-781.*

Losordo, Douglas W. et al.; "Therapeutic Angiogenesis and Vasculogenesis for Ischemia Disease: Part II: Cell-Based Therapies", 2004, American Heart Association, Circulation, vol. 109, pp. 2692-2697.*

Kureishi, Yasuko et al.; "The HMG-CoA reductase inhibitor simvastatin activates the protein Kinase Akt and promotes angiogenesis in normocholesterolemic animals", 2000, Nature Publishing Group, Nature Medicine, vol. 6, Issue 9, pp. 1004-1010.*

(Continued)

*Primary Examiner* — Devang K Thakor
*Assistant Examiner* — Ivan A Greene
(74) *Attorney, Agent, or Firm* — Oblon, McClelland, Maier & Neustadt, L.L.P.

(57) ABSTRACT

The present invention provides a novel nanotechnology-based strategy for therapeutic neovascularization. Said statin-loaded nanoparticle allows local delivery of statin and thus improves therapeutic efficacy of several kind of diseases which may treated by statin such as ischemic neovascularization.

12 Claims, 10 Drawing Sheets

(56) References Cited

U.S. PATENT DOCUMENTS

| | | | |
|---|---|---|---|
| 5,202,327 A | | 4/1993 | Robl |
| 5,250,435 A | | 10/1993 | Cover et al. |
| 5,256,689 A | | 10/1993 | Chiang |
| 5,260,332 A | | 11/1993 | Dufresne |
| 5,262,435 A | | 11/1993 | Joshua et al. |
| 5,273,995 A | | 12/1993 | Roth |
| 5,276,021 A | | 1/1994 | Karanewsky et al. |
| 5,283,256 A | | 2/1994 | Dufresne et al. |
| 5,286,895 A | | 2/1994 | Harris et al. |
| 5,302,604 A | | 4/1994 | Byrne et al. |
| 5,317,031 A | | 5/1994 | MacConnell et al. |
| 5,356,896 A | | 10/1994 | Kabadi et al. |
| 5,369,125 A | | 11/1994 | Berger et al. |
| 5,385,932 A | | 1/1995 | Vickers |
| 5,565,215 A | * | 10/1996 | Gref .................. A61K 9/0019 424/451 |
| 5,622,985 A | | 4/1997 | Olukotun et al. |
| 5,674,893 A | | 10/1997 | Behounek et al. |
| 5,902,805 A | | 5/1999 | Breton et al. |
| 7,842,716 B2 | * | 11/2010 | Serebruany ................ 514/423 |
| 2005/0037075 A1 | * | 2/2005 | Farokhzad ........ A61K 48/0041 424/468 |
| 2005/0171032 A1 | * | 8/2005 | Solomon ........................ 514/28 |
| 2005/0215618 A1 | * | 9/2005 | Serebruany .......... A61K 31/225 514/423 |
| 2005/0245433 A1 | * | 11/2005 | Chan et al. ........................ 514/3 |
| 2005/0255164 A1 | | 11/2005 | Liu et al. |
| 2006/0078531 A1 | * | 4/2006 | Sota ........................ 424/78.14 |
| 2011/0027371 A1 | * | 2/2011 | Cooper .................. A61K 9/146 424/489 |
| 2012/0004293 A1 | * | 1/2012 | Zale .................... A61K 9/5153 514/449 |

FOREIGN PATENT DOCUMENTS

| | | |
|---|---|---|
| WO | 03/103640 | 12/2003 |
| WO | 2005/072709 | 8/2005 |
| WO | WO 2005071019 A1 * | 8/2005 |
| WO | WO 2005120496 A2 * | 12/2005 |
| WO | 2007/103366 | 9/2007 |

OTHER PUBLICATIONS

Soppimath, Kumaresh S. et al.; "Biodegradable polymeric nanoparticles as drug delivery devices", 2001, Elsevier, Journal of Controlled release, vol. 70, pp. 1-20.*

Carl J Vaughan, Michael B Murphy, Brendan M Buckley; "Statins do more than just lower cholesterol", The Lancet, vol. 348, Issue 9034, Oct. 19, 1996, pp. 1079-1082.*

Kubo, Mitsuki et al.; "Abstract 1320: A Novel Nanotechnology-Based Strategy for Therapeutic Neovascularization: Local Delivery of Statin with Biodegradable Polymeric Nanoparticle Improves Therapeutic Efficacy of Ischemia Neovasculature", 2006, American Heart Association, Circulation, vol. 114, pp. II_250 (pp. 1-2 as supplied).*

Stedman's Medical Dictionary, 28$^{th}$ edition, entry for "ischemia," 2005, Lippincott, Williams & Wilkins, p. 1.*

Hankey, Graeme J. et al.; "Medical Treatment of Peripherial Arterial Disease", Feb. 2006; American Medical Association, Journal of the American Medical Association, vol. 295, No. 5, pp. 547-553.*

Sata, Masataka et al.; "Statins Augment Collateral Growth in Response to Ischemia but they Do Not Promote Cancer and Atherosclerosis", American Heart Association; 2004, Hypertension, vol. 43, pp. 1214-1220.*

Panyam, Jayanth et al.; "Biodegradable nanoparticles for drug and gene delivery to cells and tissue," 2003, Elsevier; Advanced Drug Delivery Reviews, vol. 55, pp. 329-347.*

Kubo, et al., "A Novel Nanotechnology-Based Strategy for Therapeutic Neovascularization: Local Delivery of Statin with Biodegradable-Polmeric-Nanoparticle Improves Therapeutic Efficacy of Ischemic Neovasculature", Circulation, Oct. 31, 2006, vol. 114, No. 18, Suppl. II, p. 250. (Year: 2006).*

Kubo et al., "Therapeutic Neovascularization by Nanotechnology-Mediated Cell-Selective Delivery of Pitavastatin Into the Vascular Endothelium," Arteriosclerosis, thrombosis, and vascular biology 29.6 (2009): 796-801, (DOI: 10.1161/ATVBAHA.108.182584), pp. 1-5, as provided. (Year: 2009).*

Hara et al., "The effect of poly (aspartic acid-co-lactic acid) nanospheres on the lung metastasis of B16BL6 melanoma cells by intravenous administration," Oncology Reports, vol. 16, 2006, pp. 1215-1220.

Supplementary European Search Report dated Jun. 28, 2010 in corresponding European Application No. EP 07 80 6403.

C. Astete et al., "Synthesis and characterization of PLGA nanoparticles", Journal of Biomaterials Science, Polymer Edition, vol. 17, No. 3, 2006, pp. 247-289.

K. Avgoustakis, "Pegylated poly(lactide) and poly(lactide-co-glycolide) nanoparticles: preparation, properties and possible applications in drug delivery", Current Drug Delivery, vol. 1, No. 4, 2004, pp. 321-333.

Chinese Office Action dated Aug. 16, 2010 in corresponding Chinese Application No. 200780031931.6 (with English translation).

International Search Report dated Dec. 4, 2007 in the International (PCT) Application PCT/JP2007/066926 of which the present application is the U.S. National Stage.

Weis et al., "Statins Have Biphasic Effects on Angiogenesis", Circulation, 2002, vol. 105, pp. 739-745.

Katsumoto, et al., "New 3-hydroxy-3 methyl glutaryl coenzyme A (HMG-CoA) reductase inhibitor, pitavastatin has biphasic effect on angiogenesis", Atherosclerosis Supplements, 2003, vol. 4, Issue 2, p. 203, 3P-0644.

Song et al., "Arterial uptake of biodegradable nanoparticles for intravascular local drug delivery: Results with an acute dog model", Journal of Controlled Release, 1998, vol. 54, pp. 201-211.

Avgoustakis, et al., "Effect of copolymer composition on the physicochemical characteristics, in vitro stability, and biodistribution of PLGA-mPEG nanoparticles", International Journal of Pharmaceutics, 2003, vol. 259, pp. 115-127.

Kubo, et al., "A Novel Nanotechnology-Based Strategy for Therapeutic Neovascularization: Local Delivery of Statin with Biodegradable-Polmeric-Nanoparticle Improves Therapeutic Efficacy of Ischemic Neovascularization", Circulation, Oct. 31, 2006, vol. 114, No. 18, Suppl. II, p. 250.

Kensuke Egashira, The Japanese Vascular and Medicine Organization: Joint Symposium 1 Molecular Mechanism Relating to Vascular Homeostasis—For New Therapeutic Strategy, "5. Development of Less-invasive Vascularization Therapy by Statin Topical Delivery Using Vascular Endothelial Cell Targeting Nano-DDS", Japan Atherosclerosis Society Sokai Gakujutsu Shukai Program Shorokushu, Jun. 27, 2007, p. 162.

Kubo et al., A Novel Nanotechnology-Based Strategy for Therapeutic Neovascularization: Local Delivery of Statin with Biodegradable-Polmeric-Nanoparticle Improves Therapeutic Efficacy of Ischemic Neovascularization, Circulation Journal, Mar. 1, 2007, vol. 71, Supplement 1, p. 298.

Seto et al., "Simvastatin Recovers Alveolar Bone Loss in Rat Experimental Periodontitis", The Japanese Society of Periodontology Gakujutsu Taikei Program Oyobi Koen Shorokushu, vol. 49, Shukigo, Sep. 30, 2006, p. 23 [050103].

Official Action dated Aug. 30, 2011, with English translation, issued in Japanese Application corresponding to present U.S. Application.

* cited by examiner

Figure 11 no treatment    Pitavastatin only    Pitava-loaded PLGA

PHARMACEUTICAL COMPOSITION CONTAINING STATIN-ENCAPSULATED NANOPARTICLE

CROSS REFERENCE TO RELATED APPLICATION

The present application claims priority to U.S. provisional application No. 60/840,950, filed Aug. 30, 2006.

FIELD OF THE INVENTION

The present invention provides a novel nanotechnology-based therapeutic strategy for neovascularization. Said statin-loaded nanoparticles allow local delivery of statin and thus improves therapeutic efficacy for several kind of diseases which may be treated by statin such as ischemic neovascularization.

BACKGROUND OF THE INVENTION

Statin inhibits HMG-CoA reductase, which is a rate-determining enzyme in biosynthesis of cholesterol at the liver. Thus, statin enhances uptake of cholesterol from blood into liver, resulting in significant reduction of cholesterol concentration in blood and serum triglyceride level. Statin includes, for example, pravastatin, simvastatin, fluvastatin, atorvastatin, pitavastatin, rovastatin and the like, in particular Lipitor (™).

Recent studies have shown that, in addition to treatment of hyperlipidemia, statins are useful in treatment of acne and/or skin aging (cf. Patent Reference 1); can increase nitric oxide(NO)-mediated vasodilation and blood vessel relaxation (cf. Patent Reference 2); and can help prevent a second and additional myocardial infarctions thereafter (cf. Patent References 3 and 4).

Also, statins can be used to promote angiogenesis in tissues, and such statins are useful for treating conditions in which new blood vessel growth is desirable (cf. Patent Reference 5). This includes; (1) increasing the number and function of endothelial progenitor cells (EPCs); (2) stimulating incorporation of EPCs into ischemic/injured tissues; and (3) accelerating regeneration/healing of damaged tissues.

REFERENCES

Patent Reference 1: U.S. Pat. No. 5,902,805
Patent Reference 2: WO 99/18952
Patent Reference 3: U.S. Pat. No. 5,674,893
Patent Reference 4: U.S. Pat. No. 5,622,985
Patent Reference 5: W001/93806

SUMMARY OF THE INVENTION

However, these beneficial effects have been obtained as a result of "systemic" administration of statins and observed exclusively at doses extremely higher than those used in the ordinary clinical settings. On administering statin "systemically", there is a problem of increased risk of adverse effects caused by statin, such as rhabdomyolysis and hepatic disorder. Accordingly, there is a need for "local" administration of a clinically acceptable amount of statin in order to avoid or reduce such adverse effects.

The inventor now has found that statin may be delivered via nanoparticles using biodegradable polymeric nanoparticle technology, and the nanoparticle-mediated local delivery of statin at a clinical dose range improves therapeutic effect on ischemic neovascularization. The term "local" administration, used herein, means not only the topical administrations such as transdermal or ophthalmic administration, but also an oral administration to cause the drug substance delivered selectively to, for example, ischemic tissues and other tissues to be locally treated.

The statin-loaded nanoparticles of the present invention may show prolonged intracellular release of statin in a specific tissue and a therapeutic effect stimulating neovascularization without potential side effects such as rhabdomyolysis and hepatic disorder.

BRIEF DESCRIPTION OF THE DRAWINGS

FIG. 5 shows histological appearance of hindlimb muscle on day 14 after hindlimb ischemia. In atorvastatin-loaded nanoparticle group, significant increase of CD31 positive cells is shown by immunostaining against CD31, which is endothelial marker, suggesting increased angiogenesis. Only atorvastatin and only PLGA is comparable to no-treatment group.

FIG. 6 shows histological assessment of hindlimb muscle on day 14 after hindlimb ischemia. In atorvastatin-loaded nanoparticle group, significant increase of CD31 positive cells is shown by immunostaining against CD31, which is endothelial marker, suggesting increased angiogenesis. Only atorvastatin and only PLGA is comparable to no-treatment group.

FIG. 7 shows histological appearance of hindlimb muscle on day 14 after hindlimb ischemia. In atorvastatin-loaded nanoparticle group, significant increase of vascular structure having diameter of over 20 μm is shown, suggesting increased functional angiogenesis. Only atorvastatin and only PLGA is comparable to no-treatment group.

FIG. 8 shows histological assessment of hindlimb muscle on day 14 after hindlimb ischemia. In atorvastatin-loaded nanoparticle group, significant increase of vascular structure having diameter of over 20 μm is shown, suggesting increased functional angiogenesis. Only atorvastatin and only PLGA is comparable to no-treatment group.

FIG. 11 shows histological appearance of hindlimb muscle on day 14 after hindlimb ischemia. In pitavastatin-loaded nanoparticle group, significant increase of CD31 positive cells is shown by immunostaining against CD31, which is endothelial marker, suggesting increased angiogenesis. Only pitavastatin and only PLGA is comparable to no-treatment group.

FIG. 12 shows histological assessment of hindlimb muscle on day 14 after hindlimb ischemia. In pitavastatin-loaded nanoparticle group, significant increase of CD31 positive cells is shown by immunostaining against CD31, which is endothelial marker, suggesting increased angiogenesis. Only pitavastatin and only PLGA is comparable to no-treatment group.

FIG. 13 shows histological appearance of hindlimb muscle on day 14 after hindlimb ischemia. In pitavastatin-loaded nanoparticle group, significant increase of α-SMA (α-smooth muscular actine) positive vascular structure is shown, suggesting increased functional angiogenesis. Only pitavastatin and only PLGA is comparable to no-treatment group.

FIG. 14 shows histological assessment of hindlimb muscle on day 14 after hindlimb ischemia. In pitavastatin-loaded nanoparticle group, significant increase of α-SMA (α-smooth muscular actine) positive vascular structure is shown, suggesting increased functional angiogenesis. Only pitavastatin and only PLGA is comparable to no-treatment group.

DETAILED DESCRIPTION OF THE PREFERRED EMBODIMENTS

In one aspect, the present invention provides a pharmaceutical composition comprising statin-loaded nanoparticles, wherein said statin is encapsulated in biocompatible nanoparticles.

Statins includes any compounds known as HMG-CoA (3-hydroxy-3-methylglutaryl-coenzyme A) reductase inhibitor, for example these described in U.S. Pat. Nos. 5,622,985; 5,135,935; 5,356,896; 4,920,109; 5,286,895; 5,262,435; 5,260,332; 5,317,031; 5,283,256; 5,256,689; 5,182,298; 5,369,125; 5,302,604; 5,166,171; 5,202,327; 5,276,021; 5,196,440; 5,091,386; 5,091,378; 4,904,646; 5,385,932; 5,250,435; 5,132,312; 5,130,306; 5,116,870; 5,112,857; 5,102,911; 5,098,931; 5,081,136; 5,025,000; 5,021,453; 5,017,716; 5,001,144; 5,001,128; 4,997,837; 4,996,234; 4,994,494; 4,992,429; 4,970,231; 4,968,693; 4,963,538; 4,957,940; 4,950,675; 4,946,864; 4,946,860; 4,940,800; 4,940,727; 4,939,143; 4,929,620; 4,923,861; 4,906,657; 4,906,624; and 4,897,402. In particular preferred are pravastatin (U.S. Pat. No. 4,346,227), simvastatin (U.S. Pat. No. 4,444,784), fluvastatin (U.S. Pat. No. 4,739, 073), atorvastatin (U.S. Pat. No. 5,273,995), pitavastatin, lovastatin (U.S. Pat. No. 4,231,938) and lipitor(™), especially pitavastatin and atorvastatin. The disclosures of which patents are incorporated herein by reference.

The nanoparticles of the present invention may be loaded with one or more statin(s). Alternatively, the nanoparticles of the present invention may be loaded with one or more statin(s) together with other pharmaceuticals. Said other pharmaceuticals are neovascular agents, antibiotics, anti-inflammatory agents, vitamins or pharmaceuticls other than those which are not desirable to be co-administered with statins.

Nanoparticles of the present invention are prepared from biocompatible polymers such as biocompatible polyesters. The term "biocompatible polyester" includes any polyesters prepared by polymerizing one or more monomers, not limited to, but including D,L-lactide, D-lactide, L-lactide, D,L-lactic acid, D-lactic acid, L-lactic acid, glycolide, glycolic acid, ε-caprolactone, ε-hydroxy hexanoic acid, γ-butyrolactone, γ-hydroxybutylic acid, δ-valerolactone, δ-hydroxy valeric acid, hydroxybutylic acid, malic acid, etc. In a preferred embodiment, the biocompatible polymer is poly lactic acid, poly glycolic acid, lactic acid-glycolic acid copolymer or lactic acid-asparagine acid copolymer, especially PLGA or PEG/CS-PLGA (polyethylene glycol/chitosan derivative of PLGA).

The term "PLGA", used herein, means copolymer of lactic acid or lactide and glycolic acid or glycolide in any ratio of, for example, 1:99 to 99:1, preferably 3:1. They are known also as polylactide-glycolide copolymers. PLGA may be prepared synthetically from any monomer by using conventional methods or commercially available. PLGA which may be commercially available, includes, for example, PLGA 7520 (lactic acid:glycolic acid=75:25, mean molecular weight: 20,000, Wako Junyaku, Japan). PLGA containing 25 to 65% by weight of lactic acid and glycolic acid is preferred, because it is amorphous and soluble in an organic solvent such as acetone.

Polymers mat have various mean chain lengths, resulting in a variety of intrinsic viscosities and polymeric properties. Preferred polymers in the present invention are less irritating, less toxic to organisms, biocompatible and biodegradable such that after administration it will be degraded and metabolized. Preferably, nanoparticles prepared from biocompatible polymers may release statins during a prolonged period. Among such polymers, preferred are those having, for example, 5,000 to 200,000, preferably 15,000 to 25,000 of molecular weight.

Preferably, the surface of biocompatible polymer may be modified by polyethylene glycol (PEG), resulting in increased affinity of water-soluble statins to the polymers, which affords easier encapsulation.

The statin-loaded nanoparticles of the present invention may have an average particle size of less than 1,000 nm, preferably 2.5 to 1,000 nm, more preferably 5 to 500 nm, still more preferably 25 to 300 nm, most preferably 50 to 200 nm by number when determined by the light scattering method. Said statin-loaded nanoparticles may be prepared by any methods, preferably by the spherical crystallization method. In the spherical crystallization method, spherical crystalline particles may be designed by controlling the generation and growth of crystalline particles at the final stage of synthetic route of the compounds, such that the crystals are processed under controlling directly the property. One of the spherical crystallization methods is the emulsion-solvent diffusion method (the ESD method).

Briefly, in the ESD method, two kinds of solvents, i.e. (1) a good solvent which may dissolve biocompatible polymers as a base polymer which encapsulates the drug substance and (2) a poor solvent which does not dissolve biocompatible polymers, are used. The good solvent is an organic solvent which may dissolve biocompatible polymers and may be mixed with the poor solvent. The good solvent and the poor solvent may be selected depending on the kind of statins, etc. As the solvents, though not necessarily limited to, those being safer to human beings and causing lower environmental burden, because the nanoparticles of the present invention would be used as materials for the pharmaceutical formulations.

Such poor solvents may include water or surfactant-added water such as aqueous polyvinyl alcohol solution containing polyvinyl alcohol as a surfactant. Surfactants other than polyvinyl alcohol may include lecithin, hydroxymethyl cellulose, hydroxypropyl cellulose, etc. In case where an excess amount of polyvinyl alcohol remains, the residual polyvinyl alcohol may be removed by centrifugation or other means after the solvent has been removed by evaporation.

Such good solvents may include poorly water-soluble organic solvents having a low boiling point such as halogenated alkanes, acetone, methanol, ethanol, ethyl acetate, diethylether, cyclohexane, benzene, toluene, etc. Preferably acetone or mixture of acetone with ethanol may be used, because they may have lower adverse effects to the environment and human body.

Initially, the biocompatible polymer is dissolved in a good solvent, and then a drug substance is added to the solution in a manner not to cause the biocompatible polymer precipitated. The mixture of the polymer and the drug substance in the good solvent is added dropwise to a stirred poor solvent so that the good solvent is rapidly dispersed into the poor solvent. As a result, the good solvent phase is emulsified in the poor solvent to form liquid particles of submicron sizes. The organic solvent in the emulsion particles is continuously dispersed into the poor solvent. Through the cross-dispersion of the good solvent and the poor solvent, the biocompatible polymer and the drug substance lose their solubility to eventually form spherical crystalline polymer nanoparticles encapsulating the drug substance.

Preferably, the drug loaded nanoparticles may contain the drug substance at a ratio from 0.1 to 99% (w/v), preferably from 0.1 to 30% (w/v), and more preferably from 1 to 10% (w/v). The drug substance may include one or more statins and optionally other pharmaceuticals.

By using the spherical crystalline method, the nanoparticles can be prepared by physicochemical means, and there is no need to consider the residual catalysts or starting materials, because particles of almost spherical shape are formed with a narrow distribution of particle sizes. Then, the organic good solvent may be removed by centrifugation or evaporation under reduced pressure to obtain the drug-loaded nanoparticles in powder form. So obtained powder is directly, or if desired, after conversion to re-dispersible aggregate powder by lyophilization or other means (complexing step) to provide complex powder, filled in a container to obtain statin-loaded nanoparticles.

In order to increase the loading rate of statin in nanoparticle, a cationic polymer may be added to the poor solvent. It is believed that the cationic polymer added to the poor solvent may be adsorbed to the surface of nanoparticles and inhibit leakage of the statin into the poor solvent by interacting with the statin existing on the surface of the particles.

The cationic polymers may include, but not limited to, chitosan and chitosan derivatives, cationized cellulose which is cellulose carrying a number of cationic groups, polyamino compounds such as polyethylene imine, polyvinyl amine or polyallylamine, polyamino acid such as polyornithine or poly lysine, polyvinyl imidazole, polyvinyl pyridinium chloride, alkylamino methacrylate quaternary salt copolymer (DAM), alkylamino methacrylate quaternary salt-acrylamide copolymer (DAA) and the like, preferably chitosan and its derivatives.

Chitosan is a natural polymer and is a large molecule made of glucosamine, which is a sort of aminosugar. It may be characterized by, among others, emulsion stabilizing activity, shape retaining property, biodegradability, biocompatibility, anti-bacterial activity, etc., and used as an additive in the wide range of products such as cosmetics, foods, clothing, or pharmaceuticals. Statin-loaded nanoparticles of less adverse effect and enhanced safety may be produced by adding such chitosan to the poor solvent.

In addition, a cationic lipid such as DOTAP may be added to the good solvent to form a complex with a nucleic acid compound in order to increase its affinity and dispersion stability in the good solvent. However, the amount of the cationic lipid to be used should be carefully determined, because it may cause cytopathy, when released in the cells.

The nanoparticles so obtained may be converted into a redispersible aggregate powder (nanocomposit) by powderization through lyophilization, etc. In such a case, the nanoparticles may be redispersiably complxed with an organic or inorganic substance and dried. For example, by using a sugar alcohol or sucrose, variation of the loading rate may be effectively controlled. Easiness of handling would be improved due to the sugar alcohol functioning as a filler. The sugar alcohols include, but not limited to, mannitol, trehalose, sorbitol, erythritol, maltitol, xylitol, etc., preferably trehalose.

By the conversion, the nanoparticles are converted to aggregates of easy handling and they may be reconstituted into highly reactive nanoparticles prior to use by contacting them with water. Alternatively, instead of lyophilization, the nanoparticles may converted into a complex by the fluid bed drying granulation method (using, for example, Aggromaster AGM, Hosokawamicron, Japan) to form redispersible aggregates.

The statin-loaded nanoparticles of the present invention may be used for treatment or prevention of conditions associated with HMG-CoA reductase, which conditions may be characterized, for example, by insufficient vascularization (or predisposition thereto) of the affected tissues, i.e., conditions in which neovascularization is needed to achieve sufficient vascularization in the affected tissue, and that are selected from the following group of conditions or diseases: (1) diabetic ulcers, (2) gangrenes, (3) surgical or other wounds requiring neovascularization to facilitate healing; (4) Buerger's syndrome; (5) hypertension (including pulmonary hypertension); (6) ischemic diseases including, but not limited to, cerebrovascular ischemia, renal ischemia, pulmonary ischemia, limb ischemia, ischemic cardiomyopathy, myocardial ischemia, ischemia of tissues such as muscle, brain, kidney and lung; hypertension; ulcers (e. g., diabetic ulcers); surgical wounds and other conditions characterized by a reduction in microvasculature. In preferred embodiments, conditions that can be treated in accordance with this invention are conditions that the therapeutic angiogenesis is indicated to, especially ischemia.

In the context of the present invention, "treatment" includes prevention and treatment of conditions.

Since the statin-loaded nanoparticles of the present invention can be taken up into endothelial cells, leucocytes, cardiac muscle cells and fibroblast cells, the statin-loaded nanoparticle of the present invention may be applied to certain intractable diseases. Therefore in broader aspect of the present invention, the statin-loaded nanoparticles may also be used for treatment of severe familial hypercholesteremia, pulmonary hypertension, arterial sclerosis, aortic aneurysm, neurodegenerating disease, Alzheimer's disease, cerebrovascular-type dementia, fibrosis of organs and malignant tumors.

In a further aspect, the present invention relates to a drug delivery system comprising statin-loaded nanoparticles of the present invention for prevention or treatment of diseases and/or conditions which may be treated by statin.

According to the particular finding of the present invention, the present invention also provides a method for treating diseases and/or conditions which may be treated by statins, wherein said method comprises administering to warm-blood animals (including human) in need thereof a therapeutic effective amount of statin-loaded nanoparticles of the present invention.

A pharmaceutical composition comprising nanoparticles of the present invention is suitable for topically, enterally, for example, orally or rectally, or parenterally, in particular by intramuscular, intravenous or intraarterial injection, wherein said composition may further comprise inorganic or organic, solid or liquid pharmaceutically acceptable carriers. For example, the oral pharmaceutical composition of the present invention may comprises, in addition to the statin-loaded nanoparticles, excipients, such as lactose, dextrose, sucrose, mannitol, sorbitol, cellulose and/or glycerol, and/or lubricants, such as silicate, talc, stearic acid or salts thereof such as magnesium or calcium stearate, and/or polyethylene glycol, and/or stabilizing agents. It may be particularly formulated as tables or gelatin capsules. The tablets may additionally comprise binding agents and optionally, disintegrants, absorbants, coloring agents, flavors and sweetners. The nanoparticles of the present invention may also be used as a parenteral pharmaceutical composition or an injectable solution. Said solution may comprise in addition to the active ingredient excipients such as stabilizing agents, preserving agents, wetting agents and/or emulsifier, salts for controlling osmotic pressure and/or buffers. The pharmaceutical compositions of the present invention may be prepared by any methods known in the art. They may comprise 0.1% to 99%, especially about 1% to about 50%, preferably 1 to 20% by weight of the active ingredient.

The dose range of the nanoparticles of the present invention depends on factors known to the persons skilled in the art including, but not limited to, species of warm-blood animal, body weights and ages, modes of administration, active ingredients to be used and conditions of disease to be treated. Unless otherwise indicated, the nanoparticles of the present invention may be administered 1 to 4 times daily. In a particularly preferred embodiment, the pharmaceutical composition of the present invention may be administered by a variety of frequencies such as daily, every other day, once a week, every other week, once a month, etc. Preferably, such frequencies may depend on factors known to the person skilled in the art and be easily determined by physician, etc.

According to the present invention, the statins of the invention may be administered in their effective amounts. The effective amount is a dosage of the statins sufficient to provide a medically desirable result. In general, a therapeutically effective amount means that amount necessary to delay the onset of, inhibit the progression of, or halt altogether the particular condition being treated. A therapeutically effective amount typically varies in the range from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

EXAMPLES

Preparation of the Statin-loaded Nanoparticles
i) Atorvastatin-Loaded Nanoparticles 1.2 g of PLGA (PLGA 7520, lactic acid:glycolic acid =75:25, mean molecular weight 20,000, Wako Junyaku, Japan) and 120 mg of atorvastatin were dissolved in a mixture solution of acetone (40 mL) and ethanol (20 mL) to form a polymer solution. This solution was added dropwise to a stirred (at 400 rpm) solution of 0.5 wt % of PVA (120 mL) at 40° C. at a constant rate (4 mL/min) to provide an atorvastatin-loaded PLGA nanoparticle suspension. Subsequently, the organic solvents (acetone and ethanol) were removed under reduced pressure at 40° C. while stirring at 100 rpm. After removing the solvents over 2 hours, the suspension was filtered with a filter (32 µm of mesh size), and then the filtrate was freeze-dried overnight to provide the atorvastatin-loaded PLGA nanoparticles. The loading amount of atorvastatin was 6.3% (w/v) in the nanoparticles.

The nanoparticles loaded with fluorescein isothiocyanate (FITC) loaded PLGA were prepared analogously using FITC instead of atorvastatin. The loading amount of fluorescein isothiocyanate was 5% (w/v) in the nanoparticles.

ii) Atorvastatin-loaded PEG/CS-PLGA 1.2 g of peg-PLGA (lactic acid:glycolic acid=75:25, mean molecular weight 22,900, molecular weight of peg portion 6,000, Absorbable Polymers International) and 120 mg of atorvastatin were dissolved in a mixture solution of acetone (40 mL) and ethanol (20 mL) to form a polymer solution. This solution was added dropwise to a stirred (at 400 rpm) solution of 0.04 wt % of chitosan (Moiscoat PX, N-[2-hydroxy-3-(trimethylammonio)propyl]chitosan chloride, Katakura Chikkarin) (120 mL) at 40° C. at a constant rate (4 mL/min) to provide an atorvastatin-loaded peg-PLGA nanoparticle suspension. Subsequently, the organic solvents (acetone and ethanol) were removed under reduced pressure at 40° C. while stirring at 100 rpm. After removing solvents over 2 hours, the suspension was filtered with a filter (32 μm of mesh size) to provide atorvastatin-loaded PEG/CS-PLGA nanoparticles. The loading amount of atorvastatin was 8.8% (w/v) in the nanoparticles. The nanoparticles loaded with the fluorescein isothiocyanate (FITC) loaded PEG/CS-PLGA were prepared analogously using FITC instead of atorvastatin. The loading amount of fluorescein isothiocyanate was 2.4% (w/v) in the nanoparticles.

iii)

The pitavastatin-loaded PLGA nanoparticles and the PEG/CS-PLGA nanoparticles were prepared analogously using pitavastatin instead of atorvastatin, respectively. The loading amounts of pitavastatins were 5.5% (w/v) in the nanoparticles and 2.3% (w/v) in the PEG/CS-PLGA nanoparticles.

Animals and Experimental Protocol

The study protocol was reviewed and approved by the Committee on Ethics on Animal Experiments, Kyushu University Faculty of Medicine, and the experiments were conducted according to the Guidelines of the American Physiological Society.

i) Assessment of Atorvastatin-loaded Nanoparticles

Male C57BL/6J wild-type mice were bred and maintained in the Laboratory of Animal Experiments at Kyushu University. After anesthesia with an intraperitoneal injection of ketamine hydrochloride and xyladine hydrochloride, animals underwent surgical ligation and resection of the left femoral artery to produce unilateral hindlimb ischemia. To examine the role of statin in ischemia-induced angiogenesis, a group of Ato-mice (Ato group) received intramuscular injections of atorvastatin [0.01 mg/100 μl (0.5 mg/kg)]. A group of PLGA-Ato-mice (PLGA-Ato group) and a group of PEG/CS-PLGA-Ato-mice (PEG/CS-Ato group) received intramuscular injections of atorvastatin-loaded PLGA nanoparticles and atorvastatin-loaded PEG/CS-PLGA nanoparticles (0.16 mg/100 μl and 0.12 mg/100 μl, each containing 0.01 mg of atorvastatin), respectively. As a control, a group of PLGA-FITC-mice (FITC group) received intramuscular injections of FITC-loaded PLGA nanoparticles (0.16 mg/100 μl), a group of PEG/CS-PLGA-FITC-mice (PEG/CS-FITC group) received intramuscular injections of FITC-loaded PEG/CS PLGA nanoparticles (0.16 mg/100 μl), and another group of mice (NT group) received no treatment. Mice were injected with atorvastatin or nanoparticles into the left femoral artery and tibial muscles with a 27-gauge needle immediately after induction of hindlimb ischemia.

(i) Histological Appearance

Figure 1:
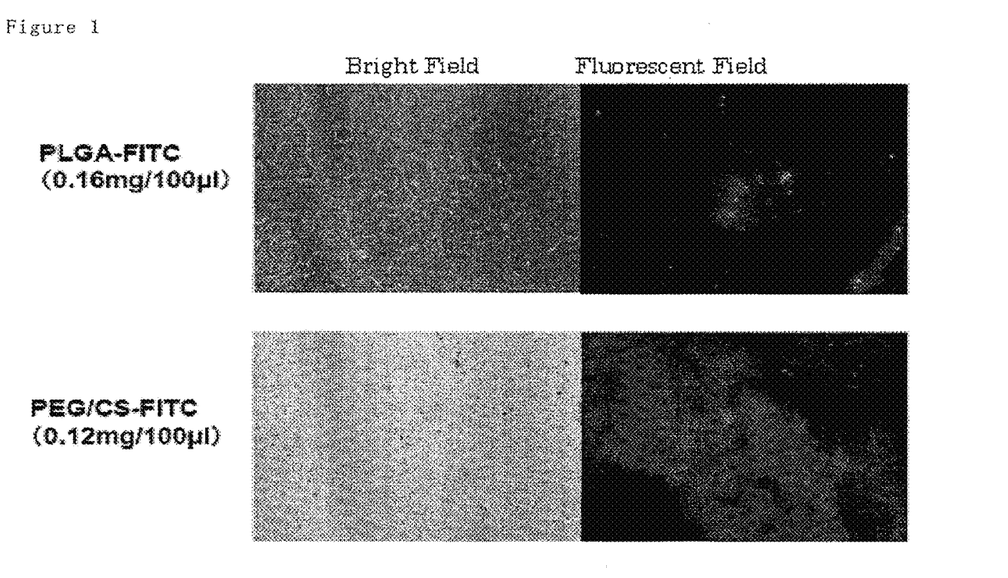
FIG. 1 shows hindlimb injected intramuscularly FITC loaded nanoparticles after induction of hindlimb ischemia. FITC loaded nanoparticles are uptaken by muscular cells and intestinal tissues, and remained over seven days.

To examine the behavior of nanoparticles after administration, muscular tissues from FITC group and PEG/CS-FITC group mice were obtained on day 7 after induction of ischemia and were observed with optical microscope and fluorescence microscope, respectively. The result is shown in FIG. 1. The fluorescence is found in both groups, thus nanoparticles remain in muscular tissues on day 7 after induction of ischemia.

(ii) Laser Doppler Perfusion Imaging

Figure 2:
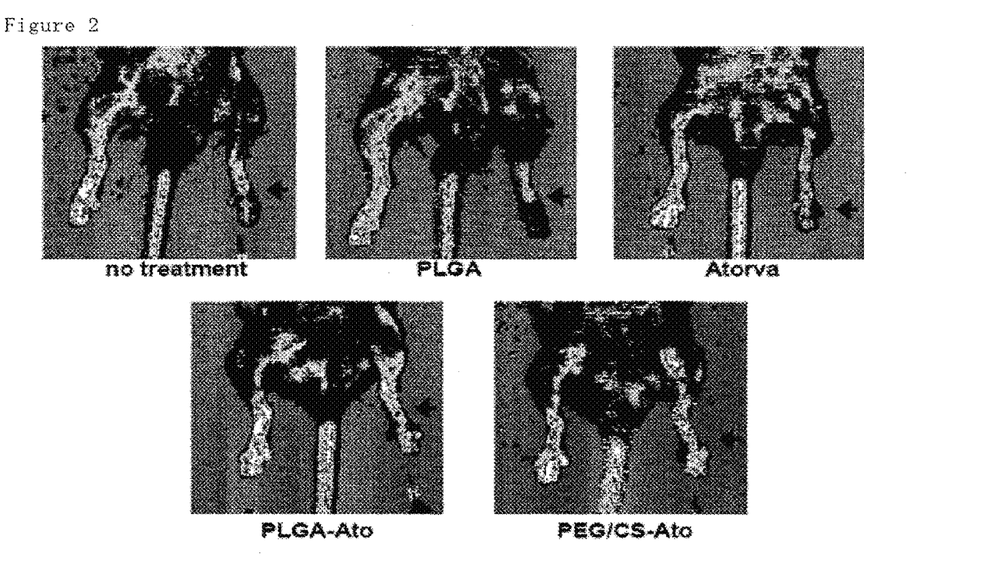
FIG. 2 shows measurements of the limb blood flow (arrowheads mean ischemic side) with Laser Doppler on day 14 after intramuscular administration of atorvastatin or corresponding amount of atorvastatin-loaded nanoparticles to ischemic hindlimb muscular after induction of hindlimb ischemia. Improved blood flow at ischemic side was obtained by atorvastatin-loaded nanoparticles.
Figure 3:
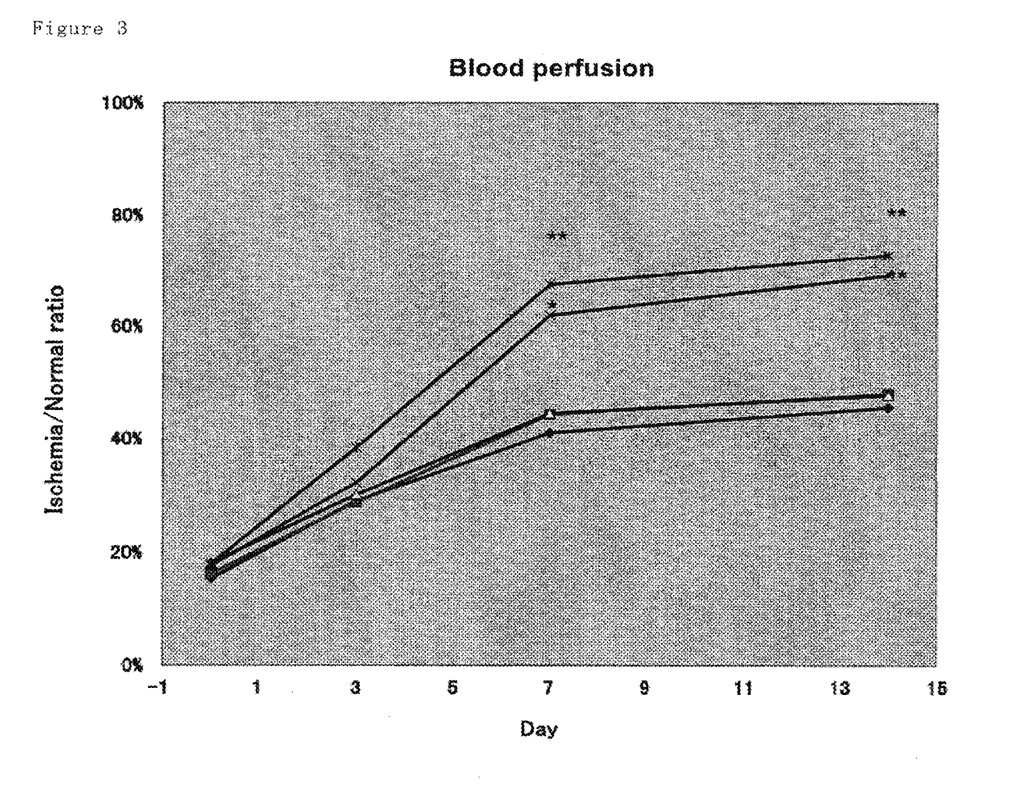
FIG. 3 shows blood flow ratios of ischemic side to normal side, wherein the blood flow of hindlimb were determined by Laser Doppler on days 0 (immediately after surgery), 3, 7 and 14. The atorvastatin-loaded nanoparticles resulted in significant improvement of blood flow after day 7. Only atorvastatin and only PLGA are comparable to no-treatment group. Against no-treatment group, *: $P<0.05$ and **: $p<0.01$, N=8 to 12. ♦: no-treatment, ■: PLGA, ▲: atorvastatin, X: PLGA-Ato, *:PEG/CS-Ato.

Measurements of the limb blood flow were performed with Laser Doppler perfusion imaging (LDPI) analyzer (Moor Instruments) on days 0 (immediately after surgery), 3, 7 and 14. The result on day 14 is shown in FIG. 2. The LDPI index was expressed as the ratio of ischemic to normal limb (shown in FIG. 3). In Ato group, PLGA group and NT group, no improvement of blood flow was shown, although in PLGA-Ato group and PEG/CS-Ato group, improvement of blood from at ischemia region was shown.

(iii) Histological Assessment on Day 14 after Ischemia

Figure 4:
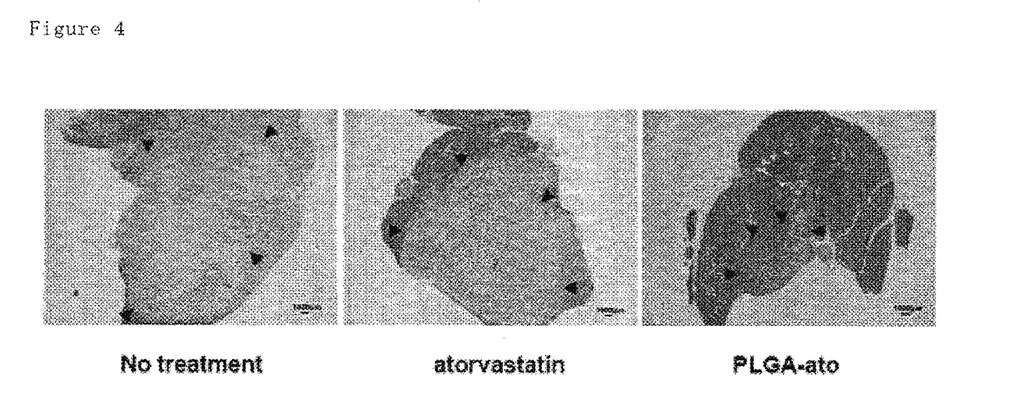
FIG. 4 shows histological appearance of hindlimb muscle on day 14 after hindlimb ischemia. In atorvastatin-loaded nanoparticle group, smaller necrosis region is shown by HE staining (region framed by arrows).

The necrosis regions of muscle tissues stained by HE were observed and compared for each groups. The result is shown in FIG. 4. Smaller necrosis region is shown at PLGA-Ato group and PEG/CS-Ato group compared with NT group or Ato group.

Figure 5:
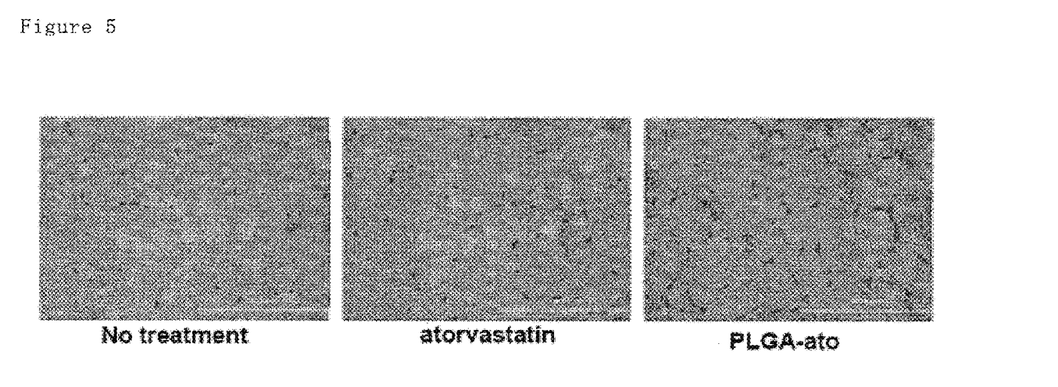
Figure 6:
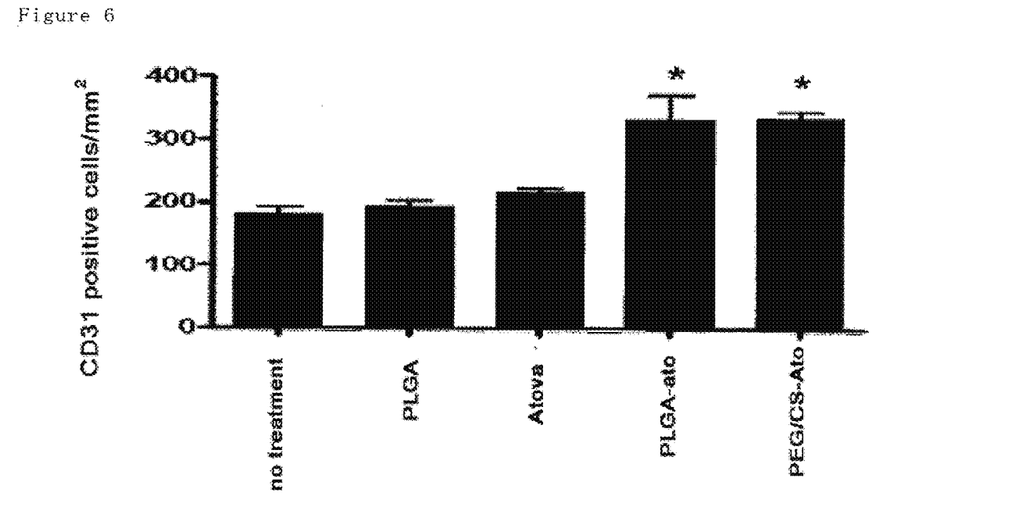

Capillary density was determined by immunohistochemical staining with anti-mouse platelet endothelial cell adhesion molecule (PECAN)-1 antibody (Santa Cruz). The results are shown in FIGS. 5 and 6. In accordance with this method, arteriolar density was determined and the results are shown in FIG. 6. Increased endothelial cells are shown at PLGA-Ato group and PEG/CS-Ato group compared with NT group or Ato group.

Figure 7:
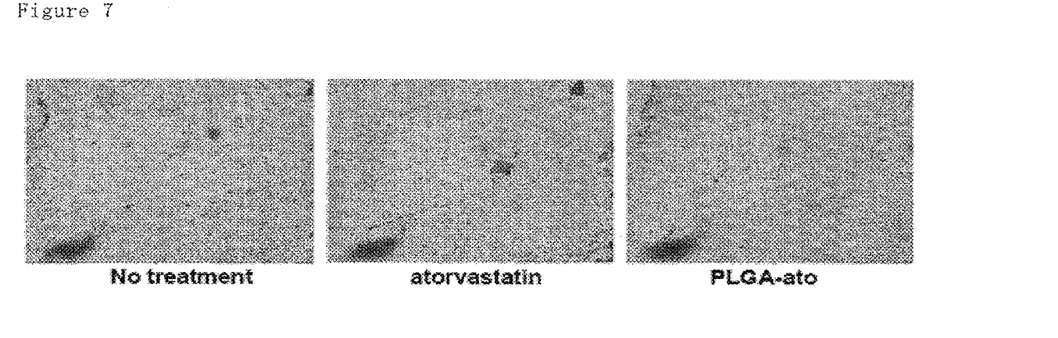
Figure 8:
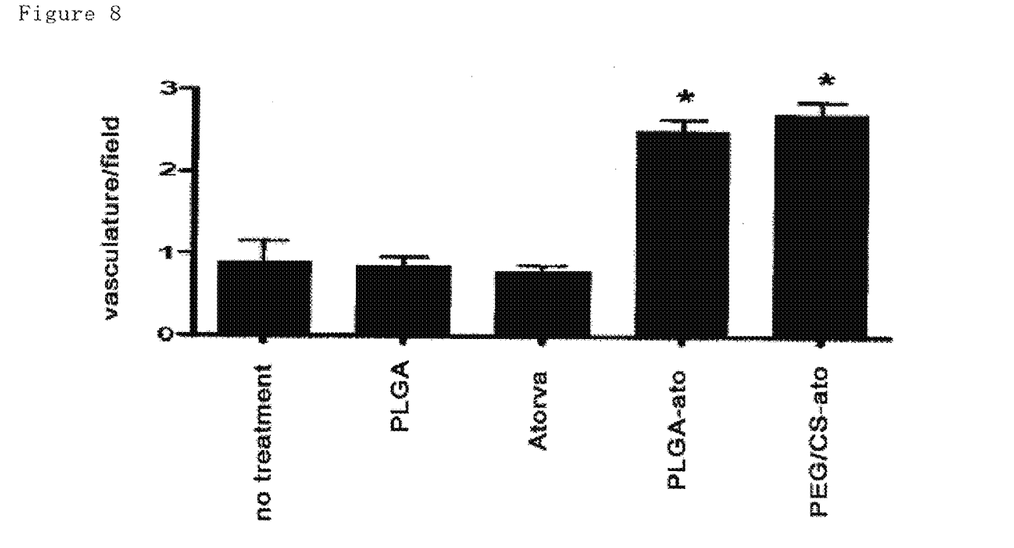

Vascular structure of diameter over 20 μm was determined. The results are shown in FIGS. 7 and 8. Increased vascular structure is shown at PLGA-Ato group and PEG/CS-Ato group compared with NT group or Ato group.

(iV) Serological Assessment

The serological assessment 14 days after hindlimb ischemia is shown in Table below. There were no difference between each group in the total cholesterol, triglyceride, myoglobin, CK, BUN and Cre values in serum. Neither group of atorvastatin nor atorvastatin-loaded nanoparticle intramuscularly injected mice showed the signs of rhabdomyolysis.

TABLE 1

|  | no treatment (n = 4) | PLGA (n = 4) | Atorva (n = 4) | PLGA-ato (n = 4) | PEG/CS-ato (n = 4) | p |
|---|---|---|---|---|---|---|
| total cholesterol (mg/dl) | 68.3 ± 1.5 | 68.3 ± 7.5 | 66.0 ± 3.2 | 80.0 ± 2.3 | 73.0 ± 4.3 | 0.21 |
| triglyceride (mg/dl) | 23.8 ± 1.9 | 31.0 ± 9.8 | 13.5 ± 1.8 | 33.3 ± 9.2 | 22.5 ± 2.2 | 0.23 |
| myoglobin (ng/ml) | <10 | <10 | <10 | <10 | <10 | — |

TABLE 1-continued

|  | no treatment (n = 4) | PLGA (n = 4) | Atorva (n = 4) | PLGA-ato (n = 4) | PEG/CS-ato (n = 4) | p |
|---|---|---|---|---|---|---|
| CK (IU/L) | 189.8 ± 30.8 | 144.5 ± 10.9 | 159.0 ± 37.7 | 91.5 ± 30.3 | 107.3 ± 16.5 | 0.13 |
| BUN (mg/dl) | 32.2 ± 3.2 | 29.3 ± 1.9 | 30.3 ± 2.8 | 23.9 ± 1.7 | 31.7 ± 5.0 | 0.39 |
| Cre (mg/dl) | 0.088 ± 0.006 | 0.090 ± 0.006 | 0.083 ± 0.009 | 0.078 ± 0.005 | 0.093 ± 0.009 | 0.57 | ii) Assessment of Pitavastatin-loaded Nanoparticles

According to the method of atorvastatin-loaded nanoparticles, after mice were anesthetized and induced ischemia, a group of Pit-mice (Pit group) received intramuscular injections of pitavastatin [0.01 mg/100 µl (0.5 mg/kg)]. A group of PLGA-Pit-mice (PLGA-Pit group) and a group of PEG/CS-PLGA-Pit-mice (PEG/CS-Pit group) received intramuscular injections of pitavastatin-loaded PLGA nanoparticles (0.18 mg/100 µl) and pitavastatin-loaded PEG/CS-PLGA nanoparticles (0.44 mg/100 µl, each containing 0.01 mg of pitavastatin), respectively. As control, a group of PLGA-mice (PLGA group) received intramuscular injections of PLGA nanoparticles (0.18 mg/100 µl) and another group of mice (NT group) received no treatment.

(i) Laser Doppler Perfusion Imaging

Figure 9:
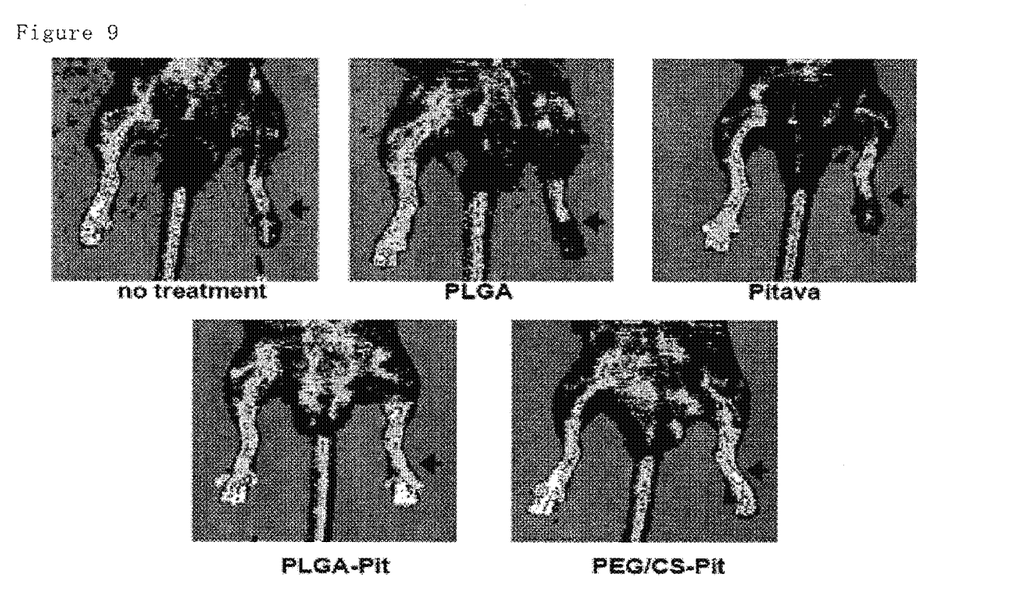
FIG. 9 shows measurements of the limb blood flow with Laser Doppler on day 14 after intramuscular administration of pitavastatin or corresponding amount of pitavastatin-loaded nanoparticles to ischemic hindlimb muscular after induction of hindlimb ischemia. Improved blood flow at ischemic side was obtained by pitavastatin-loaded nanoparticles.
Figure 10:
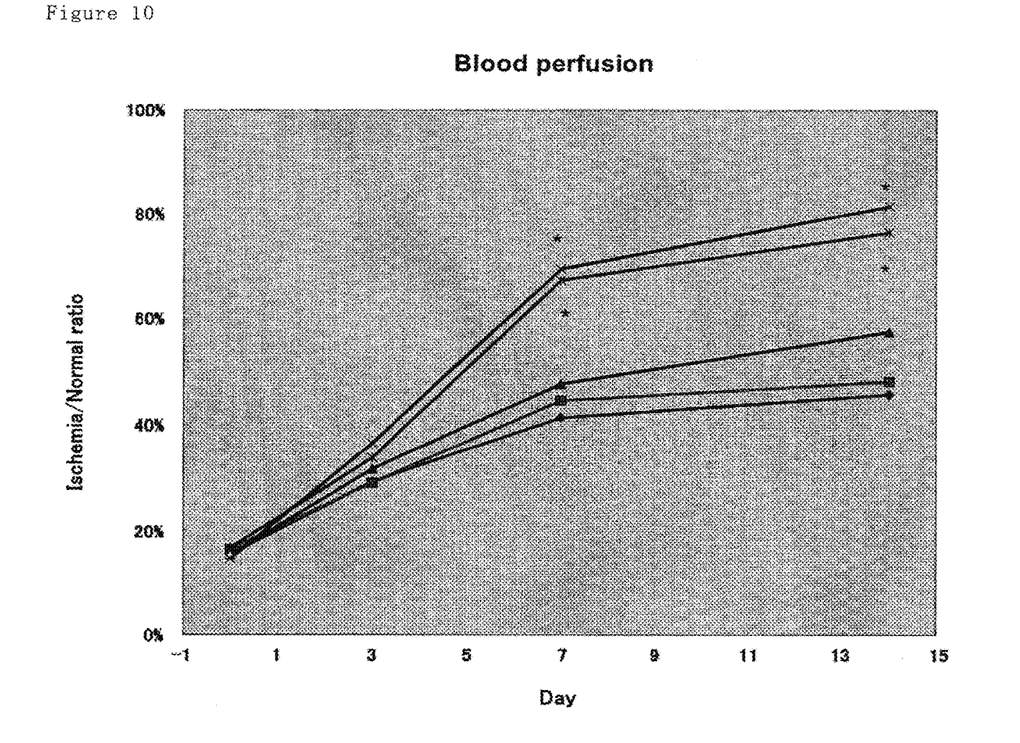
FIG. 10 shows blood flow ratios of ischemic side to normal side, wherein the blood flow of hindlimb are determined by Laser Doppler on days 0 (immediately after surgery), 3, 7 and 14. The pitavastatin-loaded nanoparticles resulted in significant improvement of blood flow after day 7. Only pitavastatin and only PLGA is comparable to no-treatment group. Against no-treatment group, *: P<0.05 and **: p<0.01, N=8 to 12. ♦: no-treatment, ■: PLGA, ▲: pitavastatin, X: PLGA-Pit, *:PEG/CS-Pit.

Measurements of the limb blood flow were performed with Laser Doppler perfusion imaging (LDPI) analyzer (Moor Instruments) on days 0 (immediately after surgery), 3, 7 and 14. The result on day 14 is shown in FIG. 9. The LDPI index was expressed as the ratio of ischemic to normal limb (shown in FIG. 10). In Pit group, PLGA group and NT group, no improvement of blood flow was shown, although in PLGA-Pit group and PEG/CS-Pit group, improvement of blood from at ischemia region was shown.

(iii) Histological Assessment Days 14 after Ischemia

Figure 11:
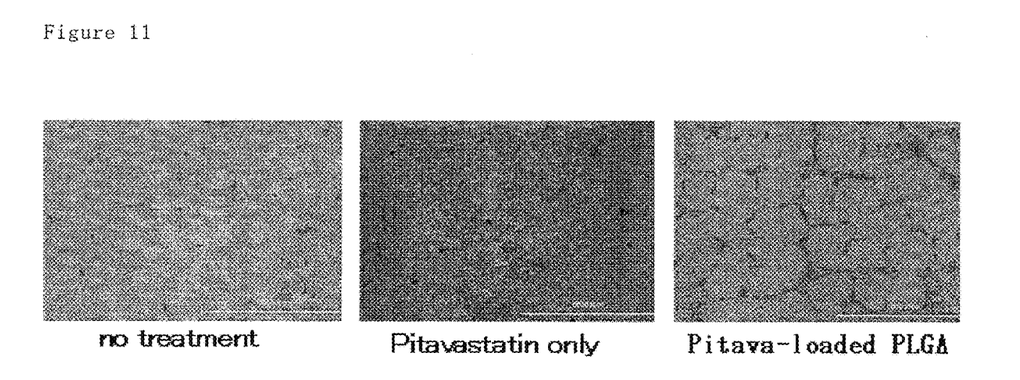
Figure 12:
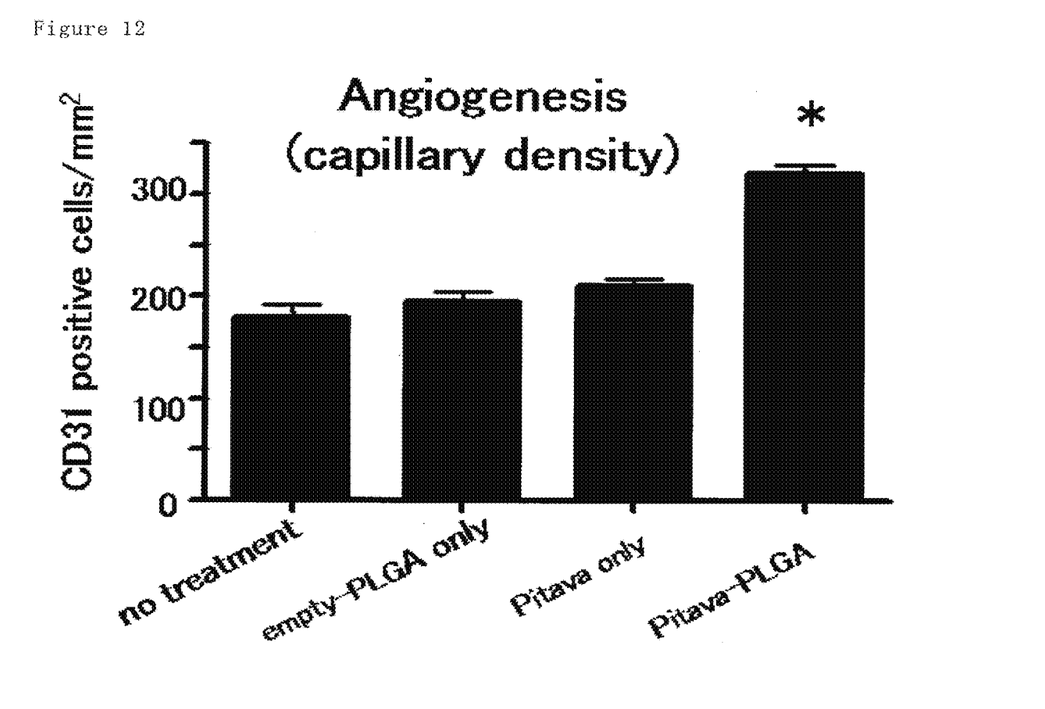

Capillary density was determined by immunohistochemical staining with anti-mouse platelet endothelial cell adhesion molecule (PECAM)-1 antibody (Santa Cruz). The results are shown in FIGS. 11 and 12. Increased endothelial cells (CD31 positive cells) are shown at PLGA-Pit group compared with NT group or Pit group.

Figure 13:
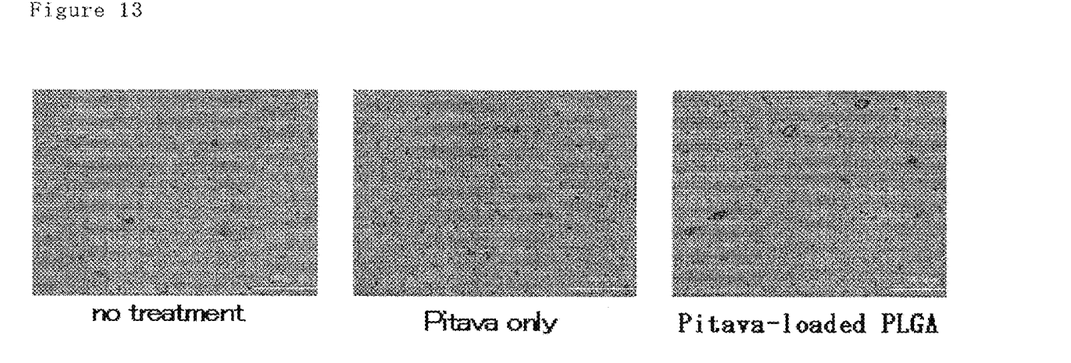
Figure 14:
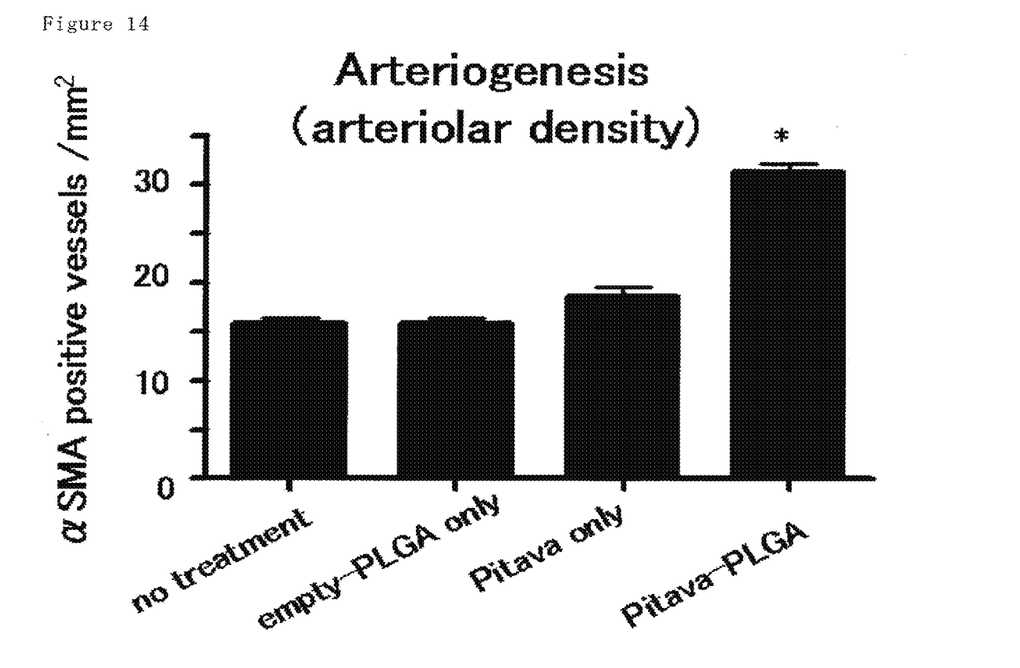

Arteriogenesis was determined by immunohistochemical staining with α-SMA. The results are shown in FIGS. 13 and 14. Increased vascular structures are shown at PLGA-Pit group compared with NT group or Pit group.

Figure 15:
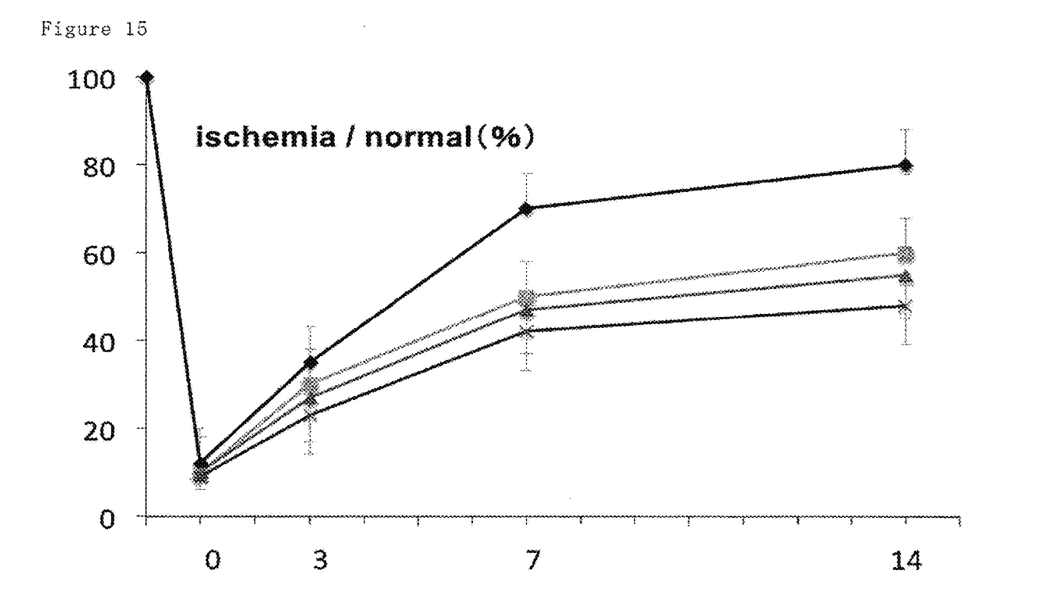
FIG. 15 shows ratios of ischemic region to normal region in hindlimb injected intramuscularly only nanoparticles, only pitavastatin (0.4, 4, 20 mg/kg) or PLGA-pitavastatin after hindlimb ischemia on days 3, 7 and 14. High dose of pitavastatin does not result in angiogenesis, while the pitavastatin-loaded nanoparticles may result in angiogenesis. ♦: PLGA-Pit, ▲: 0.4 mg/kg of pitavastatin, ■:4 mg/kg of pitavastatin, X: 20 mg/kg of pitavastatin.

The recovery rate of ischemic tissues were determined for ischemic mice injected intramuscularly with only nanoparticles, only pitavastatin (0.4, 4 and 20 mg/kg) or PLGA-pitavastatin in one portion. The result is shown in FIG. 15. No angiogenesis were shown even increased dosage of pitavastatin, while significant recovery was shown in PLGA-Pit group.

(iv) Histological Assessment 35 Days after Ischemia

Japanese rabbits (2.7 to 3.2 kg) underwent surgical ligation and resection of the unilateral femoral artery to produce hindlimb ischemia. After 7 days, animals were randomized to four groups: PLGA-pitavastatin group, PLGA-FITC group, pitavastatin group and PBS group, and received therapeutic substances by intra-ischemic-muscular injection of 5 ml (concentration of pitavastatin-loaded nanoparticle 6 mg/ml, corresponding to 0.33 mg/ml of pitavastatin). After 28 days from intramuscular injection (35 days after ischemia), animals were performed angiography. Mice were inserted catheters (5 Fr) from right internal carotid artery and the catheters were placed in left internal iliac artery under fluoroscopic control. 0.25 mg of Millisrol were injected into artery through catheters, followed by injection of imaging agents at the rate of 1 ml/second for 5 seconds to perform angiography. An assessment for the number of blood vessel was carried out by using static images at 3 second after injection of imaging agents. 5 mm of grids were prepared within the range surrounded by lower end of femur (upper end), lower end of quadriceps (lower end), arteria iliaca interna (trunks are not counted, inner end) and distal portion of severed blood vessel (outer end). Angiographic score was calculated by dividing the number of grids in which blood vessel is found by total number of grids.

Figure 16:
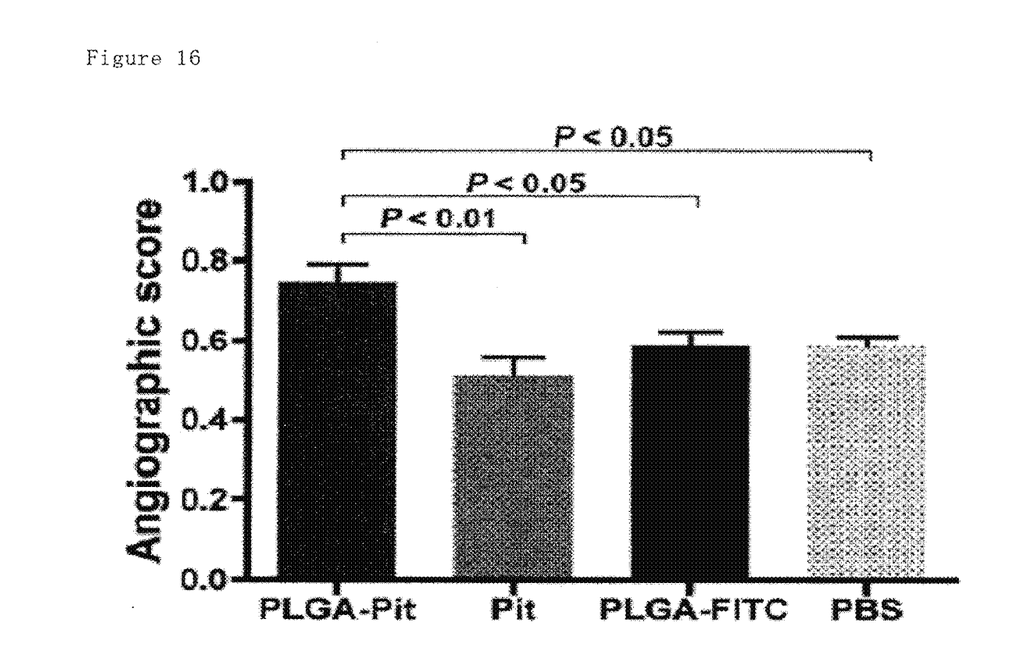
FIG. 16 shows assessment of number of vascular by using angiographic still imaging 35 days after producing ischemia.
Figure 17:
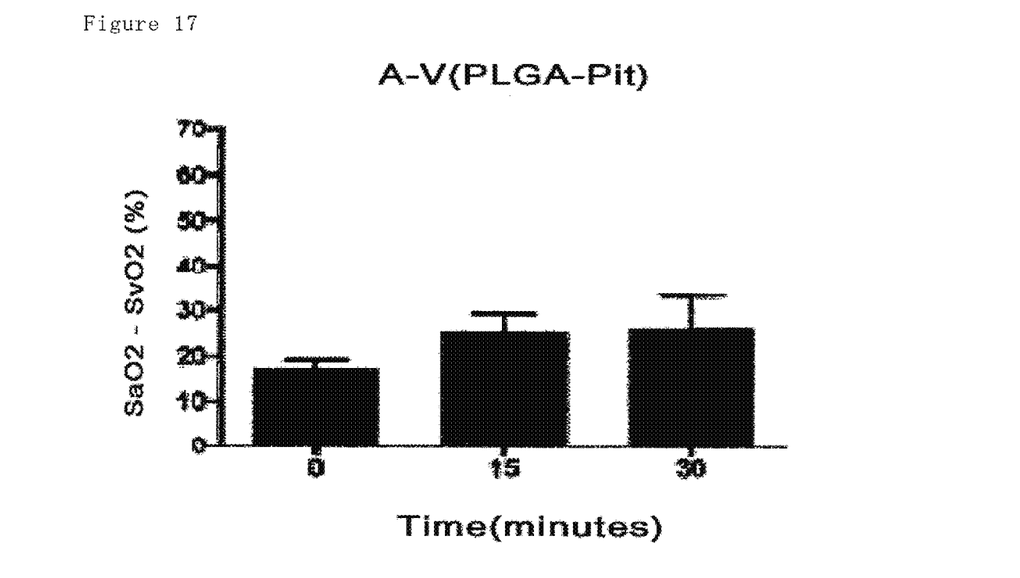
FIG. 17 shows partial pressure ratio of oxygen in arterial and venous blood among before and after muscular exercise in Japanese rabbit of PLGA-Pit group 35 days after producing ischemia. Among exercise, increases of partial pressure ratio of oxygen in arterial and venous blood were not shown.
Figure 18:
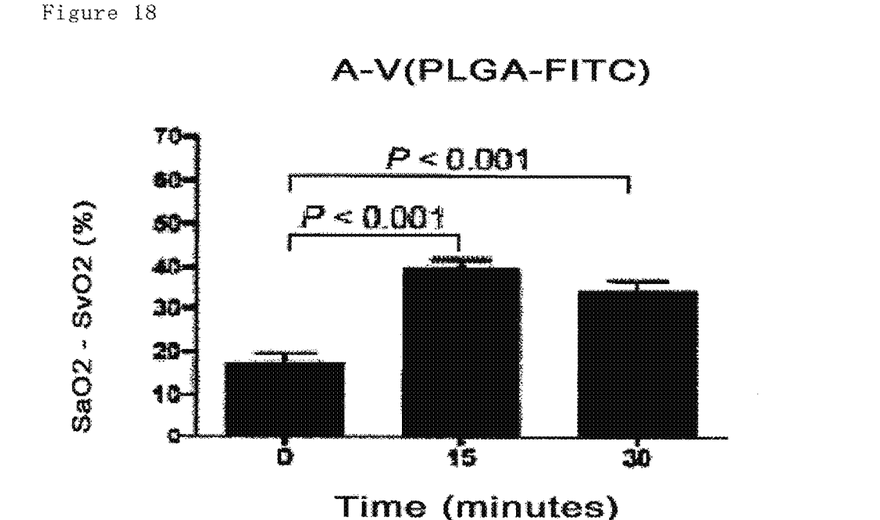
FIG. 18 shows partial pressure ratio of oxygen in arterial and venous blood among before and after muscular exercise in Japanese rabbit of PLGA-FITC group 35 days after producing ischemia. Among exercise, increases of partial pressure ratio of oxygen in arterial and venous blood were shown.
Figure 19:
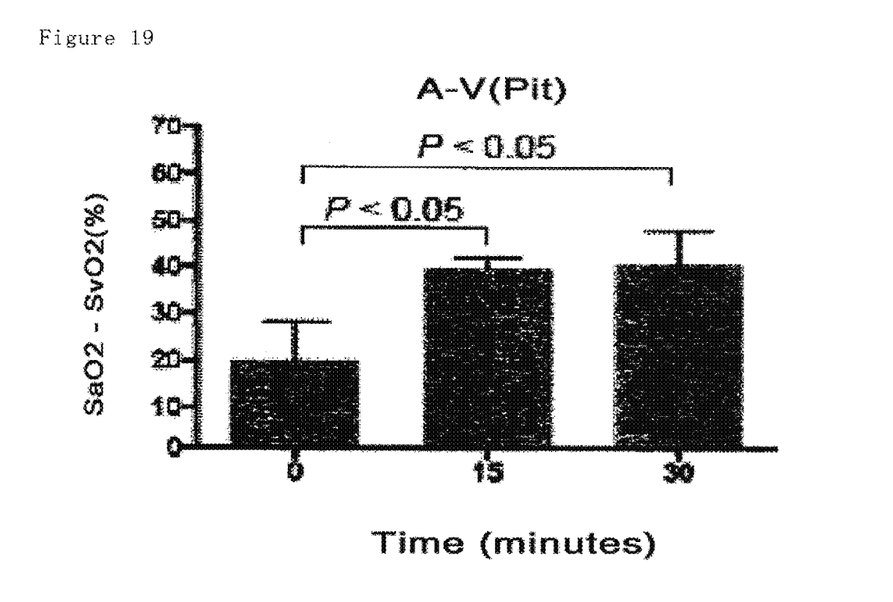
FIG. 19 shows partial pressure ratio of oxygen in arterial and venous blood among before and after muscular exercise in Japanese rabbit of Pit group 35 days after producing ischemia. Among exercise, increases of partial pressure ratio of oxygen in arterial and venous blood were shown.
Figure 20:
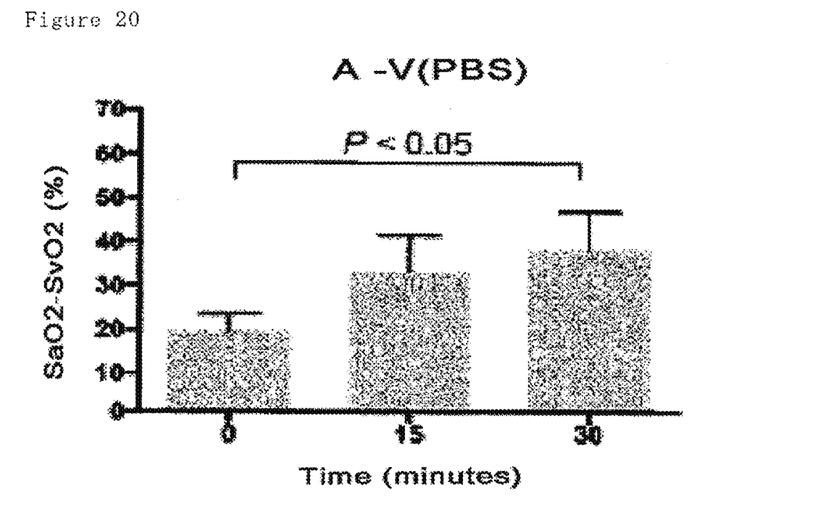
FIG. 20 shows partial pressure ratio of oxygen in arterial and venous blood among before and after muscular exercise in Japanese rabbit of no-treatment (administering PBS) group 35 days after producing ischemia. Among exercise, increases of partial pressure ratio of oxygen in arterial and venous blood were shown.

Results: Angiographic score: PLGA-Pit group; 0.74±0.04 (Mean±SE), Pit group; 0.51±0.04, PLGA-FITC group; 0.59±0.03, PBS group; 0.58±0.02 (FIG. 16). Significant increase of blood vessel was indicated in PLGA-Pit group compared with other three groups. The increase of blood vessel indicated by the angiography suggests that statin-loaded nanoparticle therapy may effectively produce angiogenesis in ischemic tissues.

The effect of nanostatin on insufficient blood from at ischemic hindlimb on muscular exercising is examined. The muscular exercise was performed by electric stimulus of muscle of ischemic hindlimb under sufficient anesthesia 35 days after induction of ischemia. The exercise was performed for 30 minutes and venous blood was collected at 0, 15 and 30 minutes and arterial blood was collected at 0 minute from ischemic hindlimb. The partial pressure ratio of oxygen in arterial and venous blood in each time point was determined. The concentration of hemoglobine was determined at 0 minute. The statistical analysis was performed by using Repeated Measures ANOVA from Bonferroni's Multiple Comparison Test. For the concentration of hemoglobine, One-way analysis of variance was used.

Results: In groups other than nanostatin group, increase of the partial pressure ratio of oxygen in arterial and venous blood during exercise was found (FIGS. 17 to 20). There is no difference between each group in the concentration of hemoglobine. According to Fick's principle, volume of blood pumped can be determined by the formula: oxygen consumption/(Hb×1.36×10×partial pressure ratio of oxygen in arterial and venous blood). Applying this principle to the present hindlimb ischemia exercise model, given the constant oxygen consumption at hindlimb muscular and from the view that there is no difference in Hb value, on exercising hindlimb, blood supplied to hindlimb is in inverse proportion to the partial pressure ratio of oxygen in arterial and venous blood. In the groups other than nanostatin group, the partial pressure ratio of oxygen in arterial and venous blood increases significantly on exercising, suggesting insufficient blood supplied, although nanostatins administration may prevent it.

(v) Local Delivery by Nanoparticles

Peripheral bloods were collected from no-ischemia mice (control) and no-treatment and pitavastation loaded nanoparticle administered group mice 14 days after ischemia. 0.5 ml of peripheral blood was hemolyzed and obtained leukocytes were then incubated together with FITC tagged anti-Sca-1 antibody (1 µg) and PE tagged anti-Flk-1 antibody (1 µg) for 30 minutes at 4° C., and served to flow cytometric analysis. Cells positive to both Sca-1 and Flk-1 were considered as vascular endothelial precursor cells (EPC) to calculate the percentage of leukocytes in peripheral blood.

Figure 21:
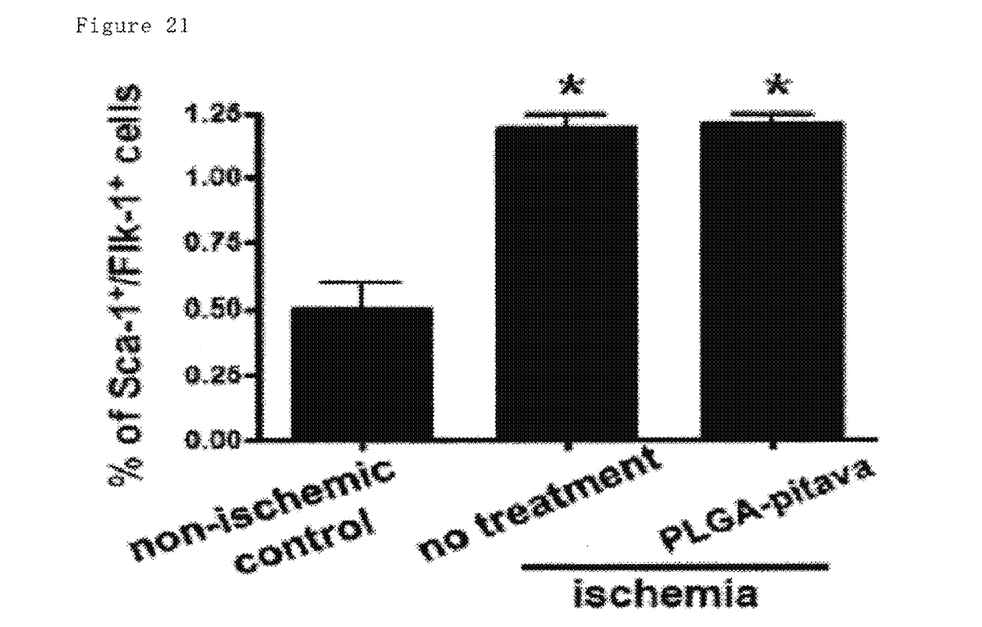
FIG. 21 shows ratio (%) of vascular endothelial precursor cells (EPCs) in leucocytes in peripheral blood from non-ischemia mice (control), as well as from no-treatment group and pitavastatin-loaded nanoparticle administered group on day 14 after producing ischemia. It is understood that angiogenic activity resulting from administration of pitavastatin-loaded nanoparticles is dominant in the ischemic region owing to local delivery rather than that observed systemically, including in bone marrow.

Results: In no-treatment group (1.19±0.05%) and statin-loaded nanoparticles group (1.21±0.03%), EPCs in peripheral blood were significantly increased compared with no-ischemia mice (0.51±0.09%). However, it was almost similar between no-treatment group and statin-loaded nanoparticles group (FIG. 21). EPCs recruited from bone marrow to peripheral blood were elevated by hindlimb ischemia, although no further elevation by statin-loaded nanoparticles was shown. From this point of view, it is understood that angiogenic, activity resulting from administration of pitavastatin-loaded nanoparticles is dominant in the ischemic region owing to local delivery rather than that observed systemically, including in bone marrow.

What is claimed is:

1. A method for treating limb ischemia, comprising:
   administering a single dose of 0.1-0.5 mg/kg of pitavastatin encapsulated in a plurality of nanoparticles to a warm-blooded animal in need thereof by intramuscular injection of a formulation comprising the nanoparticles encapsulating the pitavastatin such that the pitavastatin is selectively delivered to ischemic tissue,
   wherein each of the nanoparticles comprises a polylactide-glycolide copolymer that does not include polyethylene glycol, and
   the nanoparticles have a mean particle size of 25 to 300 nm by number.

2. The method according to claim 1, wherein the formulation further comprises polyvinyl alcohol.

3. The method according to claim 1, wherein the formulation further comprises a sugar alcohol or sucrose.

4. The method according to claim 1, wherein the nanoparticles have a mean particle size of 50 to 200 nm by number.

5. The method according to claim 2, wherein the nanoparticles have a mean particle size of 50 to 200 nm by number.

6. The method according to claim 3, wherein the nanoparticles have a mean particle size of 50 to 200 nm by number.

7. The method according to claim 1, wherein the nanoparticles comprise the pitavastatin at a ratio of from 0.1 to 30% w/v.

8. The method according to claim 5, wherein the nanoparticles comprise the pitavastatin at a ratio of from 1 to 10% w/v.

9. The method according to claim 6, wherein the nanoparticles comprise the pitavastatin at a ratio of from 1 to 10% w/v.

10. The method according to claim 1, wherein the formulation further comprises polyvinyl alcohol and one of a sugar alcohol and sucrose.

11. The method according to claim 10, wherein the nanoparticles have a mean particle size of 50 to 200 nm by number.

12. The method according to claim 11, wherein the nanoparticles comprise the pitavastatin at a ratio of from 1 to 10% w/v.

* * * * *